United States Patent
Biedermann et al.

(10) Patent No.: US 8,926,671 B2
(45) Date of Patent: Jan. 6, 2015

(54) RECEIVING PART FOR RECEIVING A ROD FOR COUPLING THE ROD TO A BONE ANCHORING ELEMENT AND A BONE ANCHORING DEVICE WITH SUCH A RECEIVING PART

(75) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 114 days.

(21) Appl. No.: 12/709,375

(22) Filed: Feb. 19, 2010

(65) Prior Publication Data
US 2010/0234902 A1 Sep. 16, 2010

Related U.S. Application Data

(60) Provisional application No. 61/154,306, filed on Feb. 20, 2009.

(30) Foreign Application Priority Data

Feb. 20, 2009 (EP) ..................................... 09002468

(51) Int. Cl.
*A61B 17/70* (2006.01)

(52) U.S. Cl.
CPC .......... *A61B 17/7037* (2013.01); *A61B 17/7032* (2013.01)
USPC ........................................................ 606/268

(58) Field of Classification Search
USPC ......... 606/246, 264, 265, 266, 267, 268, 269, 606/270
See application file for complete search history.

(56) References Cited

U.S. PATENT DOCUMENTS

| 5,672,176 A | 9/1997 | Biedermann et al. |
| 6,010,503 A | 1/2000 | Richelsoph et al. |

(Continued)

FOREIGN PATENT DOCUMENTS

| CN | 1359660 A | 7/2002 |
| EP | 0 947 174 A2 | 10/1999 |

(Continued)

OTHER PUBLICATIONS

European Search Report for European Application No. 09002468.8, Applicant Biedermann Motech GmbH, European Search Report dated May 5, 2009 and mailed May 18, 2009 (6 pgs.).

*Primary Examiner* — Anu Ramana
(74) *Attorney, Agent, or Firm* — Christie, Parker & Hale, LLP

(57) ABSTRACT

A receiving part for receiving a rod for coupling the rod to a bone anchoring element, the receiving part including: a receiving part body having a channel for receiving a rod and defining an accommodation space for accommodating a head of a bone anchoring element, the accommodation space having an opening for inserting the head; and a pressure element at least partially in the accommodation space, the pressure element including a first portion having a recess to receive the rod, and a second portion having a flexible portion to clamp the head, wherein the pressure element is moveable along a longitudinal axis of the receiving part body from an inserting position to insert the head, to a pre-locking position to clamp the head in the receiving part by a pre-stress exerted by the pressure element, to a locking position to lock the head in the receiving part.

30 Claims, 8 Drawing Sheets

(56) References Cited

U.S. PATENT DOCUMENTS

| | | | |
|---|---|---|---|
| 6,063,090 A | 5/2000 | Schläpfer | |
| 6,132,432 A | 10/2000 | Richelsoph | |
| 6,368,321 B1 * | 4/2002 | Jackson | 606/270 |
| 6,471,705 B1 * | 10/2002 | Biedermann et al. | 606/271 |
| 7,291,151 B2 | 11/2007 | Alvarez | |
| 7,322,981 B2 * | 1/2008 | Jackson | 606/266 |
| 7,604,655 B2 * | 10/2009 | Warnick | 606/265 |
| 2002/0082602 A1 | 6/2002 | Biedermann et al. | |
| 2005/0137594 A1 | 6/2005 | Doubler et al. | |
| 2006/0089644 A1 | 4/2006 | Felix | |
| 2006/0161153 A1 | 7/2006 | Hawkes et al. | |
| 2006/0173456 A1 | 8/2006 | Hawkes et al. | |
| 2007/0123862 A1 | 5/2007 | Warnick | |
| 2007/0161999 A1 | 7/2007 | Biedermann et al. | |
| 2007/0270813 A1 | 11/2007 | Garamszegi | |
| 2008/0009862 A1 | 1/2008 | Hoffman | |
| 2008/0147129 A1 | 6/2008 | Biedermann et al. | |
| 2008/0154315 A1 | 6/2008 | Jackson | |
| 2008/0183215 A1 | 7/2008 | Altarac et al. | |
| 2008/0234761 A1 | 9/2008 | Jackson | |
| 2008/0243193 A1 | 10/2008 | Ensign et al. | |
| 2008/0249576 A1 | 10/2008 | Hawkes et al. | |
| 2008/0269809 A1 | 10/2008 | Garamszegi | |
| 2008/0294202 A1 | 11/2008 | Peterson et al. | |
| 2008/0294203 A1 | 11/2008 | Kovach et al. | |
| 2009/0012567 A1 | 1/2009 | Biedermann et al. | |
| 2009/0018591 A1 | 1/2009 | Hawkes et al. | |
| 2009/0036934 A1 | 2/2009 | Biedermann et al. | |
| 2009/0062865 A1 | 3/2009 | Schumacher | |
| 2009/0062867 A1 | 3/2009 | Schumacher | |
| 2010/0198272 A1 | 8/2010 | Keyer et al. | |

FOREIGN PATENT DOCUMENTS

| | | |
|---|---|---|
| EP | 1 749 489 A1 | 2/2007 |
| EP | 1 923 011 A1 | 5/2008 |
| JP | 8-257035 | 10/1996 |
| JP | 10-225467 A | 8/1998 |
| JP | 11-318933 | 11/1999 |
| JP | 2001-505469 A | 4/2001 |
| JP | 2008-541880 A | 11/2008 |
| WO | WO 2006/127992 | 11/2006 |
| WO | WO 2007/038350 A2 | 4/2007 |
| WO | WO 2007/117366 A2 | 10/2007 |

* cited by examiner

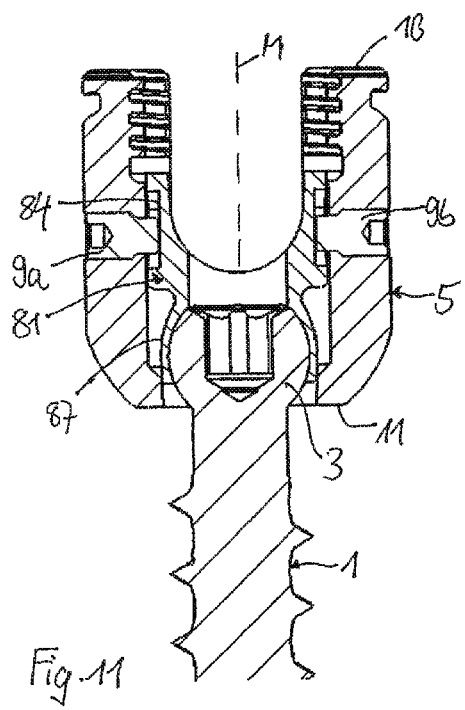
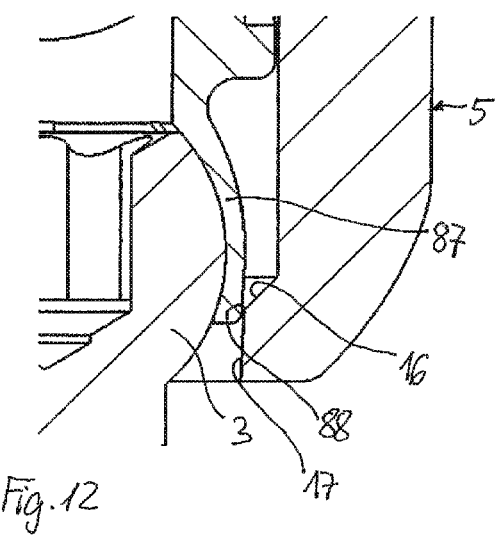
Fig. 12
Fig. 11
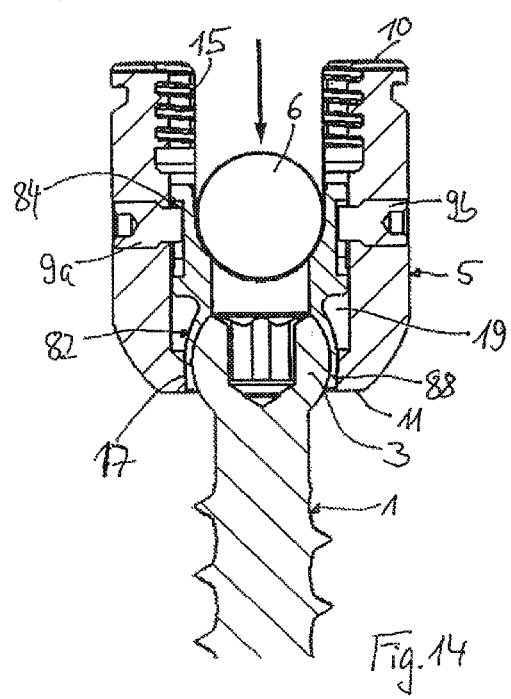
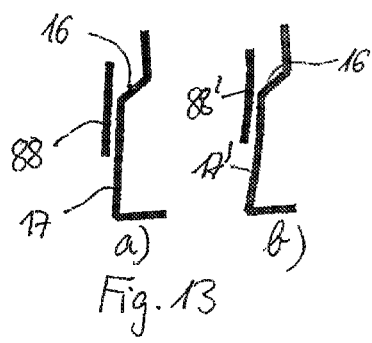
Fig. 13
Fig. 14

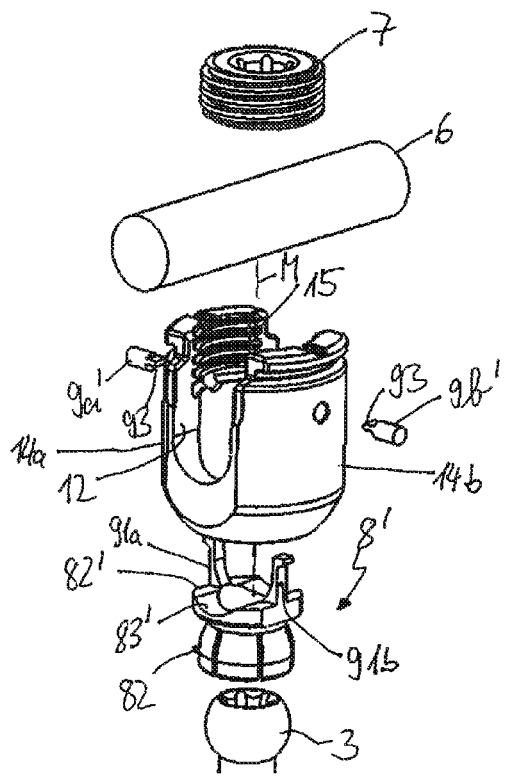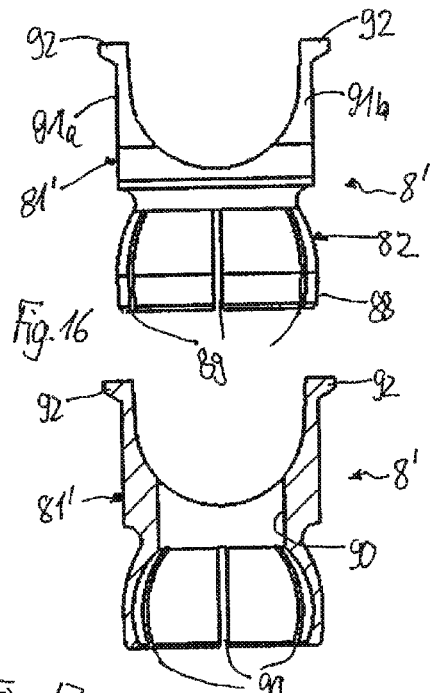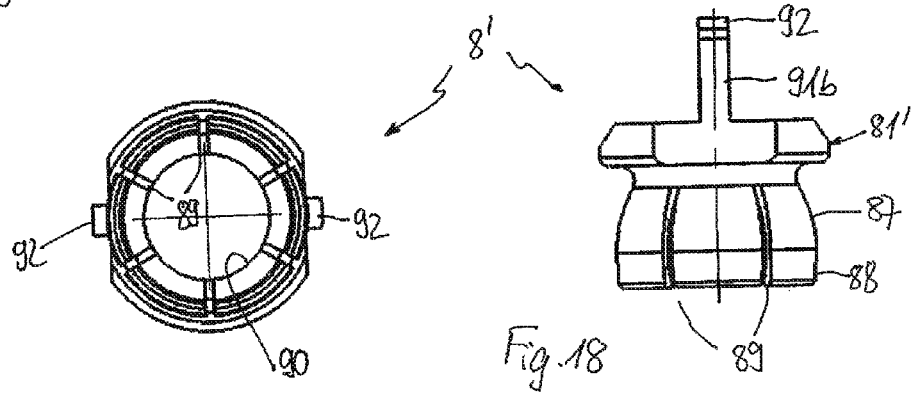

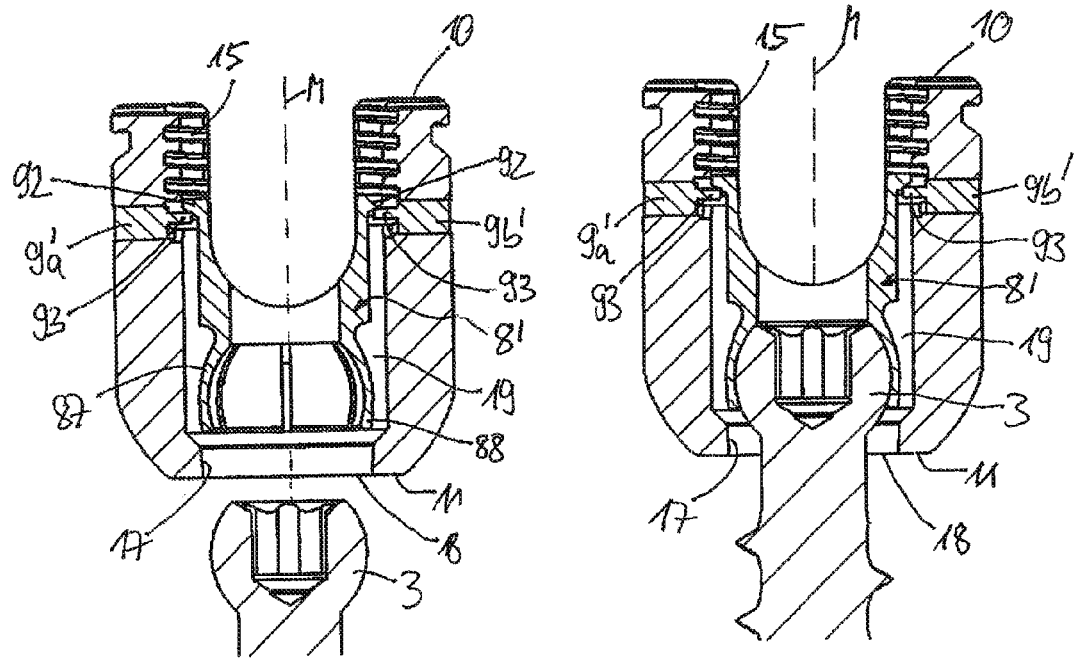
Fig. 20
Fig. 21
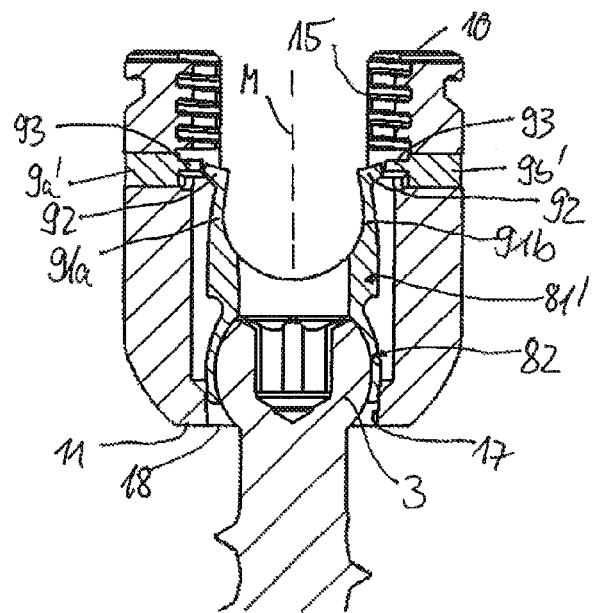
Fig. 22

RECEIVING PART FOR RECEIVING A ROD FOR COUPLING THE ROD TO A BONE ANCHORING ELEMENT AND A BONE ANCHORING DEVICE WITH SUCH A RECEIVING PART

CROSS-REFERENCE TO RELATED APPLICATION(S)

The present application claims the benefit of U.S. Provisional Patent Application Ser. No. 61/154,306, filed Feb. 20, 2009, the contents of which are hereby incorporated by reference in their entirety, and claims priority from European Patent Application EP 009 002 468.8, filed Feb. 20, 2009, the contents of which are hereby incorporated by reference in their entirety.

BACKGROUND

1. Field of the Invention

The invention relates to a receiving part for receiving a rod for coupling the rod to a bone anchoring element and a bone anchoring device with such a receiving part. The receiving part includes a receiving part body and a pressure element located at least partly in an accommodation space of the receiving part body. The pressure element has a flexible portion to clamp the head. The pressure element can assume in the receiving part body an insertion position in which introduction and removal of the head is permitted, a locking position in which the head is locked in the receiving part, and a pre-locking position in which the head is clamped by a pre-stress exerted by the pressure element.

2. Description of Related Art

Various designs of polyaxial bone screws, wherein the head is clamped from the side to lock the rotational position of the bone screw, are known.

U.S. Pat. No. 5,672,176 describes a bone screw with a receiving part with a conically shaped seat and a conically shaped pressure element which exerts a pressure onto the head from above and from the side. If the cone angle has a value laying within a specific range self-locking of the pressure element within the receiving part takes place which allows to preliminary lock the head within a receiving part while the rod is still movable in order to allow the adjustment of its position.

WO 2007/038350 A2 discloses an apparatus for connecting a bone anchor to a support rod, the apparatus including a connector body and a cap. The connector body has a socket for insertion, angulation and removal of a bone anchor. A sleeve is provided which is configured to fit over the connector body in a temporary position, in which the sleeve permits insertion of the bone anchor, to move to a provisional locking position, in which the sleeve permits angulation but prevents removal of the bone anchor, and to move to a locking position, in which the sleeve prevents both angulation and removal of the bone anchor.

U.S. Pat. No. 6,063,090 relates to a device used to connect a longitudinal support to a pedicle screw by an accommodating head having a channel to accommodate the longitudinal support. The pedicle screw and the accommodating head are connected via a conical collet chuck in the accommodating head and by a spherical head on the pedicle screw. The device allows engagement of the pedicle screw in the accommodating head after the pedicle screw has been inserted into the bone.

U.S. Pat. No. 6,132,432 describes a spinal implant fixation assembly including a bone fixation member such as a screw and a rod receiving seat which is operatively connected to the bone fixation element. In one embodiment a screw head receiving insert is provided, which is movable within the assembly between a locked position entrapping the screw head therein and an unlocked position, wherein the screw head enters or escapes.

SUMMARY

It is an object of the invention to provide an improved receiving part for receiving a rod for coupling the rod to a bone anchoring element and a bone anchoring device with such a receiving part. The receiving part may include fewer parts and may be more easily and/or more safely handled during surgery.

A pressure element can be arranged in the receiving part body in three positions. In an insertion position the head is insertable from a bottom of the receiving part body into an accommodation space of the receiving part body. In a pre-locking position, the pressure element pre-locks the head in the accommodation space, which prevents inadvertent removal of the head from the receiving part body and/or inadvertent movement of the head with respect to the receiving part body during surgery. This allows for safer handling of the bone anchoring device during surgery. In a locking position, the head is finally locked in the receiving part. The pressure element can be releasably held in the insertion position and/or in the pre-locking position. This makes handling more convenient.

Pre-locking and final locking of the head are achieved with the same pressure element. Hence, the receiving part and the bone anchoring device according to embodiments of the invention comprise fewer elements, which reduces the costs for manufacturing and which facilitates handling. It makes use of the principle of clamping the head of the bone anchoring element circumferentially from a lateral side, which reduces a force necessary to safely clamp the head. The design of the receiving part allows introduction of the head from the bottom of the receiving part. Such a design may be more readily utilized when a modular system is provided wherein various bone anchors and/or different receiving parts are available prior to surgery.

BRIEF DESCRIPTION OF THE DRAWINGS

Further features and advantages of the invention will become apparent from the description of embodiments using the accompanying drawings. In the drawings:

FIG. 11 shows a cross-sectional view of the bone anchoring device of the first embodiment with the pressure element in a pre-locking position.

FIG. 12 shows an enlarged view of a detail of FIG. 11.

FIGS. 13a to 13h show various examples of outer and inner cooperating surfaces of the pressure element and the receiving part body, respectively.

FIG. 14 shows the bone anchoring device of FIG. 8 with a rod inserted and the head locked.

FIG. 15 shows an exploded perspective view of a bone anchoring device according to a second embodiment.

FIG. 16 shows an enlarged side view of a pressure element according to the second embodiment.

FIG. 17 shows a cross-sectional view of the pressure element of FIG. 16.

FIG. 18 shows a side view of the pressure element of FIG. 16 rotated by 90°.

FIG. 19 shows a bottom view of the pressure element of FIG. 16.

FIG. 20 shows a cross-sectional view of the bone anchoring device according to the second embodiment with the pressure element in an insertion position and the bone anchoring element not yet inserted, the cross-section taken perpendicular to the rod axis.

FIG. 21 shows the bone anchoring device of FIG. 20 with the bone anchoring element fully inserted.

FIG. 22 shows the bone anchoring device of FIG. 20 with the pressure element in a position just before a pre-locking position.

DETAILED DESCRIPTION OF THE INVENTION

Figure 1:
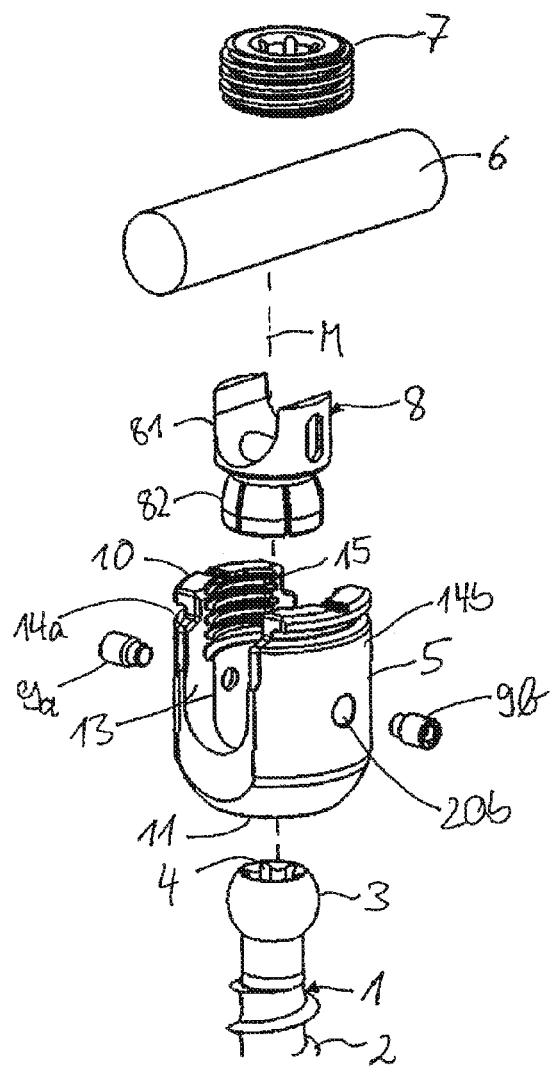
FIG. 1 shows a perspective exploded view of a first embodiment of the bone anchoring device.
Figure 2:
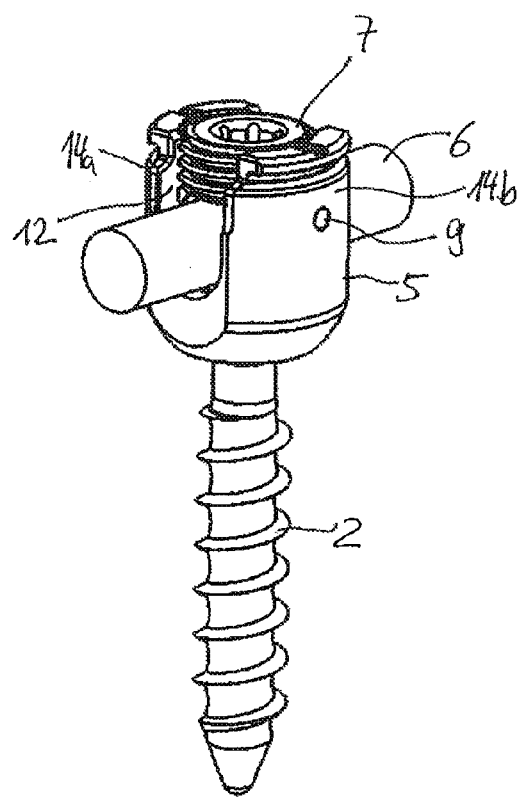
FIG. 2 shows a perspective view of the bone anchoring device of FIG. 1 in an assembled state.

As shown in. FIGS. 1 and 2, a bone anchoring device according to a first embodiment comprises a bone anchoring element 1 in the form of a bone screw having a threaded shaft 2 and a head 3, which is in this embodiment a spherical segment-shaped head. The head 3 has a recess 4 for engagement with a screwing-in tool. The bone anchoring device further comprises a receiving part body 5 for receiving a rod 6 to connect the rod 6 to the bone anchoring element 1. Further, a closure element 7 in the form of an inner screw is provided for securing the rod 6 in the receiving part body 5. In addition, the bone anchoring device includes a pressure element 8 for locking the head 3 in the receiving part body 5. The pressure element 8 is held in the receiving part body 5, for example via pins 9a, 9b.

The receiving part body 5 is now explained with reference to FIGS. 1 and 8 to 14. The receiving part body 5 comprises a first end 10 and a second end 11 opposite the first end and an axis of symmetry M passing through the first end and the second end. A bore 12 is provided which is coaxial with the axis of symmetry M. In a first region adjacent to the first end 10, the receiving part body 5 has a U-shaped recess 13, which is symmetric with respect to the axis of symmetry M, the recess 13 having a bottom directed towards the second end 11 and two free lateral legs 14a, 14b extending towards the first end 10. In the region of the legs 14a, 14b an internal thread 15, which cooperates with the inner screw 7, is provided. A channel formed by the U-shaped recess 13 is sized so as to receive the rod 6 therein, the rod to connect a plurality of anchoring devices. At a second region near the second end 11, a cylindrical portion of the bore 12 is followed by a first tapered portion 16 tapering towards the second end 11 with a cone angle. The first tapered portion 16 is followed by a second tapered portion 17 tapering towards the second end 11 with a cone angle smaller than the cone angle of the first tapered portion. An opening 18 is provided at the second end 11. A diameter of the opening 18 is larger than a diameter of the head 3 and smaller than the inner diameter of the bore 12. The coaxial bore 12 provides an accommodation space 19 for the screw head 3.

On each leg 14a, 14b, bores 20a, 20b extending through the legs 14a, 14b are provided for receiving the pins 9a, 9b. The bores 20a, 20b are located approximately at a center of each leg.

Figures 3, 4:
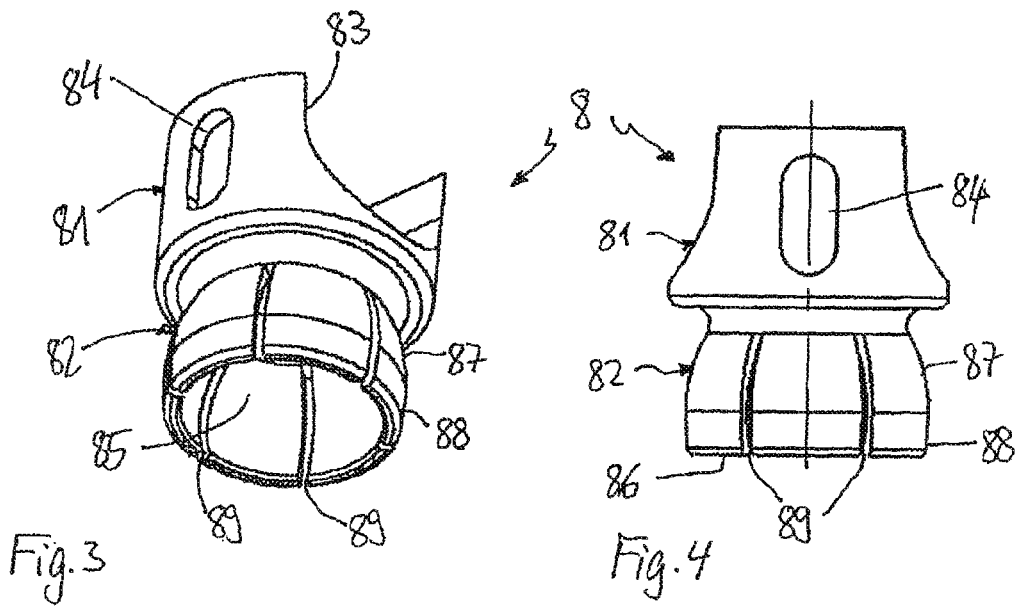
FIG. 3 shows a perspective view of a pressure element according to the first embodiment.
FIG. 4 shows a side view of the pressure element of FIG. 3.
Figures 5, 6:
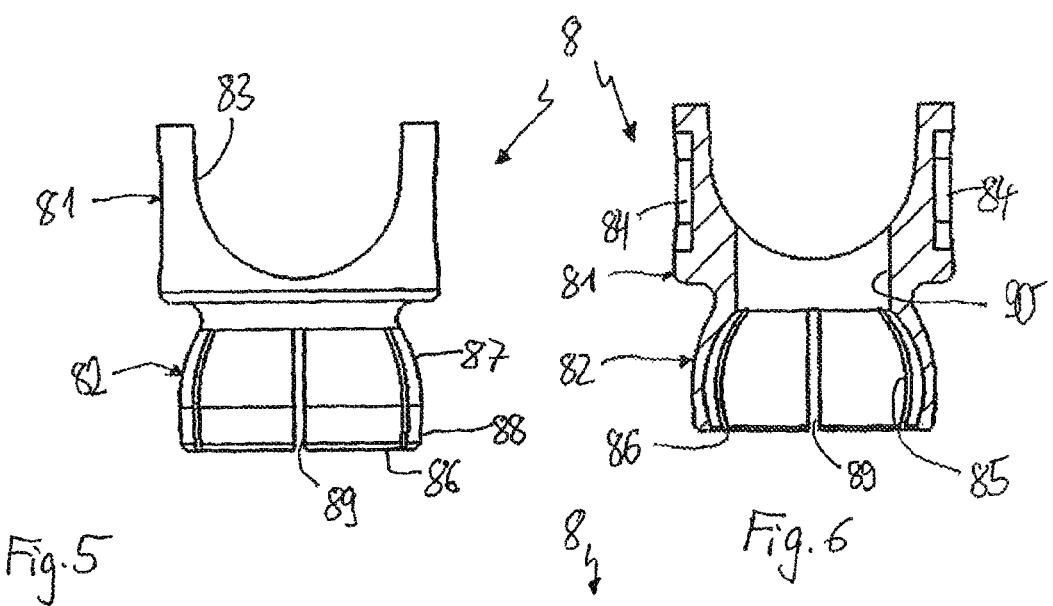
FIG. 5 shows a side view of the pressure element shown in FIG. 4 rotated by 90°.
FIG. 6 shows a cross-sectional view of the pressure element shown in FIG. 5.
Figure 7:
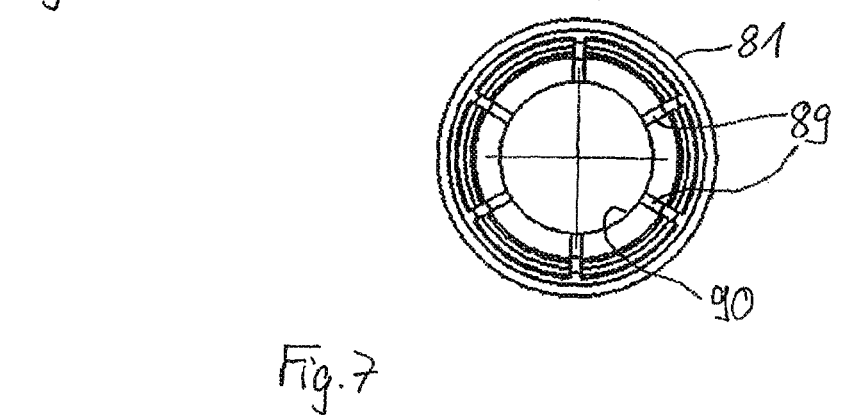
FIG. 7 shows a bottom view of the pressure element shown in FIGS. 3 to 6.

As can be seen in FIGS. 1 and 3 to 7, the pressure element 8 includes a first portion 81, which is substantially cylindrical and which has an outer diameter which is slightly smaller than the inner diameter of the bore 12, so that the pressure element 8 is movable in the bore 12, and a second portion 82 which is recessed with respect to the first portion and which has a maximum outer diameter which is smaller than the inner diameter of the bore 12. The first portion 81 has at its end opposite to the second portion 82 a U-shaped recess 83 for receiving the rod 6 therein when the pressure element 8 is situated in the receiving part body 5. At the lateral sides of the U-shaped recess the pressure element comprises two elongate recesses 84 in the outer wall which are arranged opposite to each other, and which are aligned such that a longer side of the elongate recesses 84 is parallel to the axis of symmetry M of the receiving part body 5. As can be seen in FIG. 4, the width of the lateral sides of the first portion 81 decrease towards the end opposite to the second portion 82 for at least a part of the first portion 81.

The second portion 82 is formed similar to a collar, and comprises a first end at the side of the first portion 81 which is recessed with respect to the first portion 81 and a second end, and a hollow interior 85 which is substantially spherically shaped to clamp the spherical head 3 therein. The second end of the second portion 82 has an opening 86 for introduction of the head 3. An outer wall of the second portion 82 comprises a first portion 87 which is spherical and a second portion 88 adjacent to the opening 86 which is tapered. The tapered portion 88 of the pressure element cooperates with the second tapered portion 17 of the receiving part body. The second portion 82 of the pressure element further comprises a plurality of slits 89 extending from an edge of the opening 86 through the second portion 82. The number and dimensions of the slits 89 are such that the wall of the second portion is flexible enough to snap onto the head 3 when the head 3 is being inserted. Further, the pressure element comprises a coaxial bore 90 for providing access to the screw head 3 by a tool.

As can be seen in FIGS. 8 to 14, since the pressure element has a maximum outer diameter which is slightly smaller than the inner diameter of the bore 12, it can be inserted from the first end 10 of the receiving part body 5 into the receiving part body 5. Once the pressure element 8 is inserted, the pins 9a, 9b are introduced in the bores 20a, 20b so that they engage in the elongate recesses 84, thereby holding the pressure element 8 in the receiving part body 5 and with the U-shaped recess 83 aligned with the U-shaped recess 13 of the receiving part body 5, and preventing escaping of the pressure element through the first end 10. Since the second portion 82 of the pressure element 8 has an outer diameter which is smaller than the inner diameter of the bore 12, and since the second portion 82 of the pressure element has a flexible outer wall, the second portion can expand within the accommodation space 19 when the screw head 3 is introduced.

All parts described before may be made of a bio-compatible material, such as a bio-compatible metal like stainless steel or titanium, or a bio-compatible metal alloy, for example, nitinol, or are made from a bio-compatible plastic material, for example, PolyEtherEtherKetone (PEEK).

Figures 8, 9:
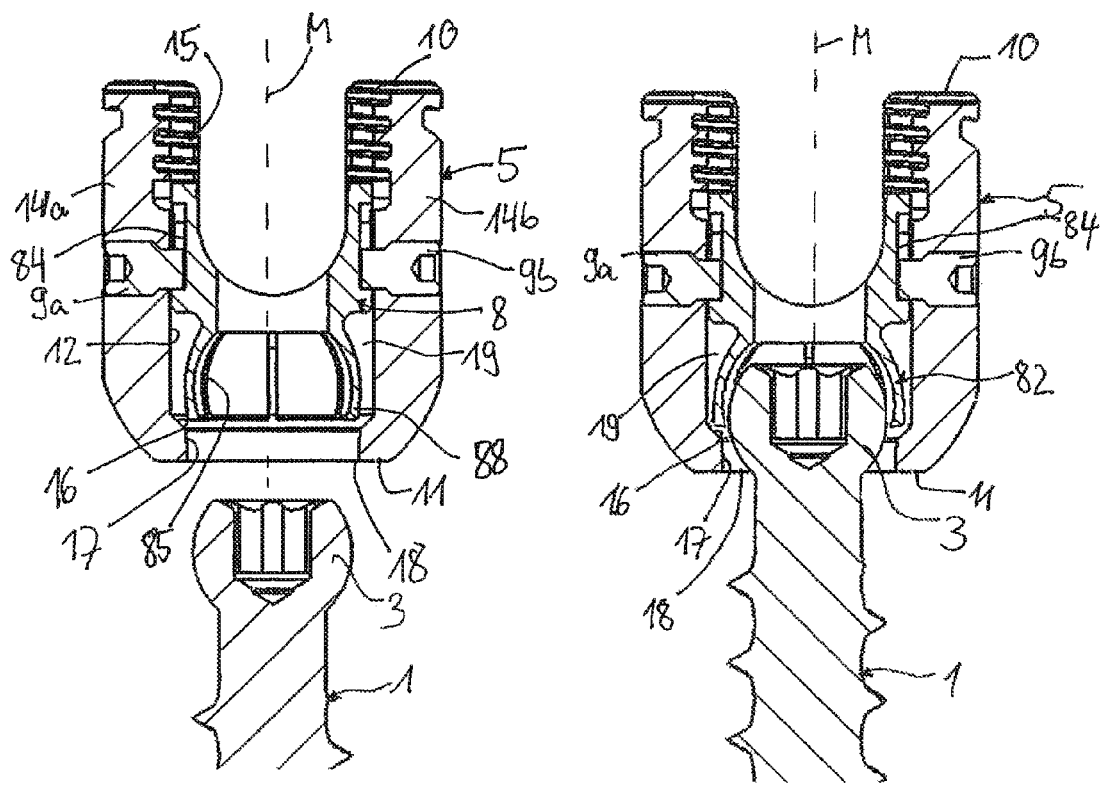
FIG. 8 shows a cross-sectional view of a bone anchoring device according to the first embodiment with a pressure element in a first position, and when the bone anchoring element is not yet inserted, the section taken perpendicular to the rod axis.
FIG. 9 shows a cross-sectional view of the bone anchoring device according to the first embodiment with the pressure element in the first position and the bone anchoring element partially inserted.
Figure 10:
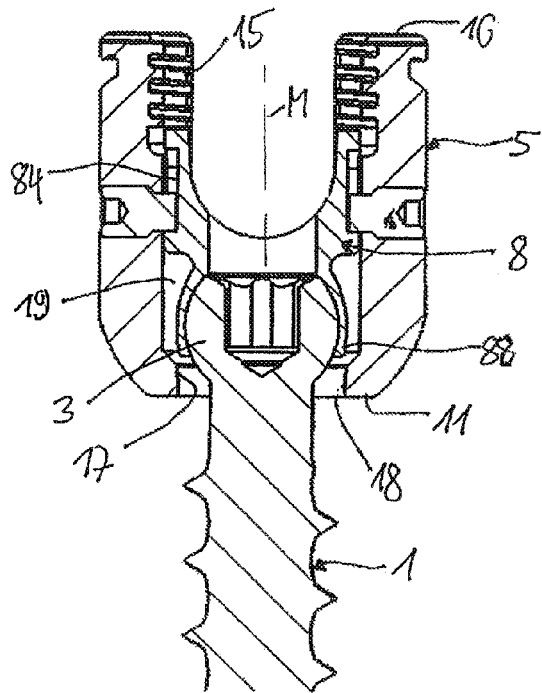
FIG. 10 shows the bone anchoring device of FIG. 9 with the bone anchoring element fully inserted.

The steps of assembling the bone anchoring device are now explained with respect to FIGS. 8 to 14. First, when the pressure element 8 is introduced into the receiving part body 5 and held by the pins 9a, 9b, it is oriented such that the opening 86 is directed towards the second end 11 of the receiving part body 5. As shown in FIG. 8, the pressure element 8 is in its uppermost position which is an insertion position for allowing the screw head 3 to be inserted. In the insertion position, the flexible second portion of the pressure element is positioned freely in the accommodation space 19. The insertion position is limited against upward movement by an abutment which is in this embodiment provided by the engagement of the pins 9a, 9b with the lower end of the recesses 84. As shown in FIG. 9, the screw head 3 is then inserted through the opening 18 into the accommodation space 19, where the second portion 82 of the pressure element 8 is located. The screw head 3 is introduced into the hollow interior 85 of the second portion 82 of the pressure element through the opening 86. Due to the flexibility of the wall provided by the slits 89, the second portion 82 expands in the accommodation space 19 as shown in FIG. 9. The second portion 82 snaps onto the screw head 3 until it encompasses the screw head 3 as shown in FIG. 10. The pins also prevent the pressure element 8 from escaping through the open first end 10 when the screw head 3 is inserted. In the insertion position the screw head 3 is pivotable in the receiving part and also removable if the pressure element remains in this position. There may be means (not shown) for holding the pressure element temporarily in the insertion position. Alternatively, the pressure element can be held in the insertion position by means of a tool (not shown).

FIGS. 11 and 12 show a pre-locking position of the pressure element. When the screw head 3 is inserted and the pressure element 8 is pressed down slightly, the outer wall of the second portion 82 of the pressure element is guided by the first tapered portion 16, so that it contacts the second tapered portion 17 of the receiving part body. The tapered portion 88 of the outer wall of the pressure element 8 and the tapered portion 17 of the receiving part body 5 come into engagement, whereby a prestress is exerted by the second portion 82 of the pressure element onto the screw head 3, which pre-locks the head 3. Pre-locking means that under conditions arising during surgery, an angular position of the bone anchoring element 1 with respect to the receiving part body 5 is maintained and can be loosened only by exerting an additional force onto the receiving part body or the bone anchoring element. The pre-locking position of the pressure element can be achieved either manually by pushing down the pressure element, or by inserting the rod and screwing in the inner screw 7 so that the rod presses onto the pressure element thereby moving it slightly downwards.

FIGS. 13a and 13b show the engagement of the outer surface portion of the pressure element and the inner surface portion of the receiving part body in the pre-locking condition. As described before, the surfaces 17, 88 can be tapered as shown in FIG. 13a. Alternatively to, or in addition to, tapered surfaces, portions of the surfaces 88', 17' can be rounded as shown in FIG. 13b. The first tapered portion 16 at the receiving part body 5 serves only for guidance in some embodiments and can be omitted.

Figure 13C:
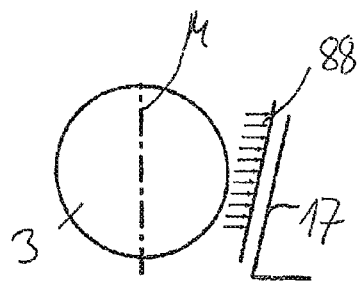
Figure 13D:
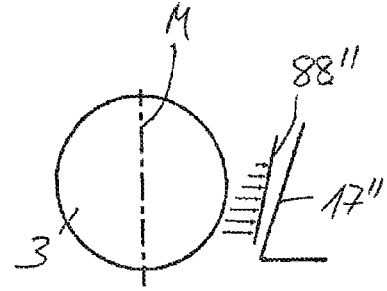
Figure 13E:
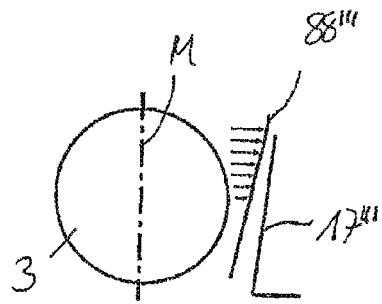
Figure 13F:
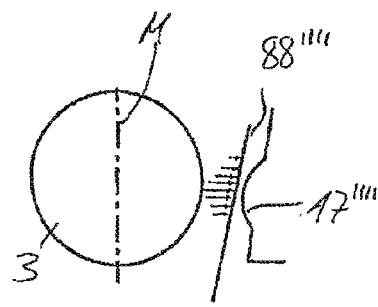

FIGS. 13c to 13h schematically show various examples of engagements of the outer surface portion of the pressure element and the inner surface portion of the receiving part body. In FIG. 13c the two tapered portions 17, 88 are tapered at substantially a same angle. This provides a substantially even pressure distribution (approximated by arrows) between the second portion 88 of the pressure element and the tapered portion 17 of the receiving part body. FIGS. 13d and 13e show two different variations where the portions are tapered at different angles. FIG. 13d shows a main contact area at the bottom of portion 17" and FIG. 13e shows a main contact area at the top of portion 17'". FIG. 13f shows a tapered portion 88"" of the pressure element and a rounded or curved portion 17"" of the receiving part body, wherein the curvature is directed towards the center of the receiving part body. With such a configuration, a focused contact area at the rounded portion can be achieved.

Figure 13G:
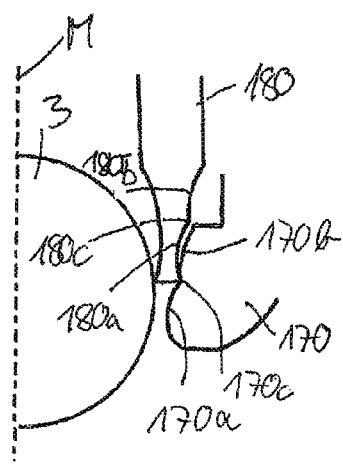
Figure 13H:
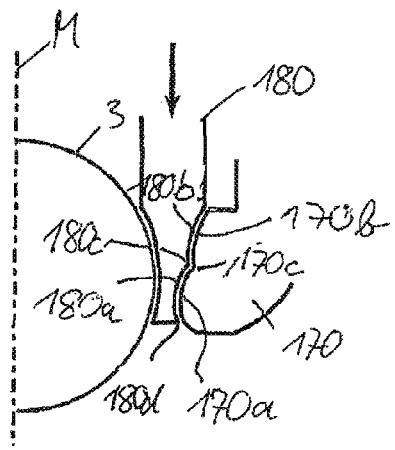

In FIGS. 13g and 13h the narrowing portion 170 of a modified example of the receiving part body 5 has a double spherical radius formed by two curved portions 170a and 170b adjacent to each other with a groove 170c therebetween. The curvatures are directed to a central axis M. A modified pressure element 180 has at its lower end two correspondingly curved portions 180a and 180b which correspond to the curved portions 170a and 170b, with a crest 180c therebetween, and an outer crest 180d at an outer edge of the pressure element 180.

As shown in FIG. 13g, when the pressure element 180 moves downwards, its lowermost edge 180d engages in the groove 170c. In this position, there is a frictional clamping of the head 3, which still allows the head 3 to be pivoted upon exertion of a force which is greater than the force needed to pivot the head 3 when the head 3 is introduced in the insertion position. This is an example of the pre-locking condition. As shown in FIG. 13h, by pressing the pressure element 180 further downward, the respective curvatures 180a, 180b of the pressure element 180 engage with the corresponding curvatures 170a, 170b of the narrowing portion 170 to lock the head 3.

The third position of, for example, the embodiment of FIG. 8, which is a locking position, is shown in FIG. 14. The locking position is defined as the position in which the screw head 3 is locked in the receiving part body 5. In this position, the tapered outer surface portion 88 of the pressure element engages the second tapered portion 17 of the receiving part body over a larger area. Thereby, the flexible wall of the second portion 82 of the pressure element 8 is pressed onto the head 3 so that the head 3 is locked. This position is achieved by further tightening the inner screw 7, thereby further pressing down the rod 6.

In use, the bone anchoring device can be, for example, pre-assembled in such a way that a suitable bone anchoring element 1 is selected and introduced into the receiving part body 5 with an inserted pressure element 8. The bone anchoring device can be brought into the pre-locking condition by slightly pushing down the pressure element 8. Then, the screw element 1 is screwed into the bone. The recess 4 of the head 3 can be accessed with a screw tool through the coaxial bore 12 and the bore 90. To correctly align the receiving part with respect to the rod to which it shall be connected, an additional force is exerted onto the receiving part either manually or by application of an instrument. Once a desired position of the rod with respect to other bone anchoring devices is achieved, the inner screw 7 is tightened, thereby shifting down the pressure element into the locking position. A final tightening of the inner screw locks the rod and the head substantially simultaneously.

The bone anchoring device can be pre-assembled either by the manufacturer or in the course or preparation of surgery, or at any other time. In one embodiment, the surgeon can select the desired receiving parts and bone anchoring elements prior to surgery according to specific details of the particular clinical application. The design of the bone anchoring device allows selection of an appropriate bone anchoring element in terms of diameter, length, and other features. Hence, a modular system is provided which includes various receiving parts and several bone anchoring elements, which then individually can be chosen and adapted.

A second embodiment of the bone anchoring device is now described with respect to FIGS. 15 to 26. Parts which are similar to those of the first embodiment have the same reference numerals, and the descriptions thereof will not be repeated. The second embodiment of the bone anchoring device differs from the first embodiment in the design of the pressure element and the pins. The first portion 81' of the pressure element 8' differs from the first portion 81 of pressure element 8. The first portion 81' of the pressure element 8' has a shallow recess 83' which is curved in a substantially cylinder segment shape for guiding the rod 6. It further includes two upstanding resilient fingers 91a, 91b extending from respective lateral sides of the recess 83' in the direction of the first end 10 of the receiving part body. The fingers 91a, 91b have outwardly directed portions 92 at their free ends, respectively. An outer diameter of the first portion 81' at least in the region of the fingers, is smaller than the inner diameter of the bore of the receiving part body, such that the resilient fingers 91a, 91b can move.

Pins 9a', 9b' each have a flattened portion 93, a width of which is substantially the same as a width of the outwardly extending portions 92 of the resilient fingers 91a, 91b. When the pins 9a', 9b' are inserted into the bores 20a, 20b, the portions 93 extend into the coaxial bore 12 of the receiving part body 5 as shown in FIG. 20. In this manner, an abutment is provided for the receiving part 8'.

Figure 23:
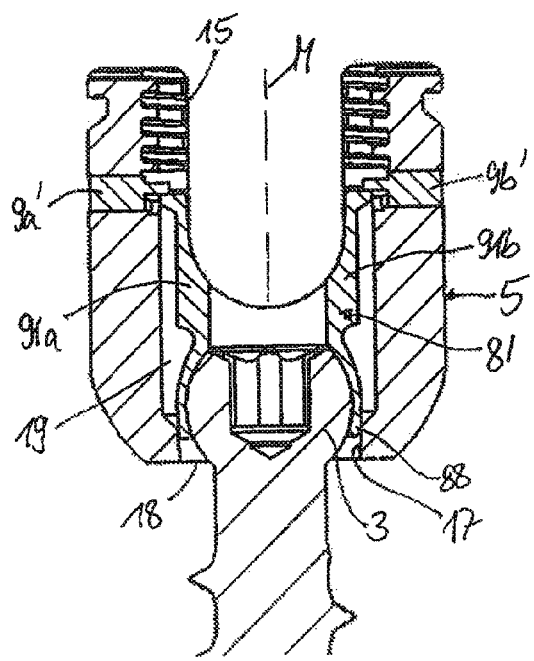
FIG. 23 shows the bone anchoring device of FIG. 20 with the pressure element in the pre-locking position.
Figure 24:
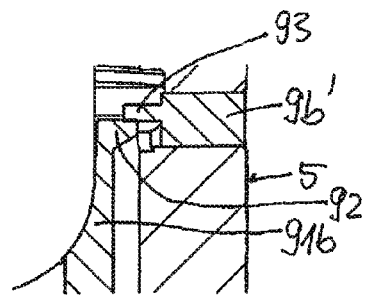
FIG. 24 shows an enlarged view of a portion of FIG. 23.
Figure 25:
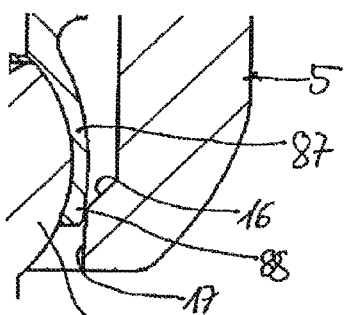
FIG. 25 shows an enlarged view of another portion of FIG. 23.

The assembly of the bone anchoring device according to the second embodiment is explained with respect to FIGS. 20 to 25. In FIG. 20, first, the pressure element 8' is inserted from the first end 10 into the receiving part body 5. Then the pins 9a', 9b' are inserted into the holes in the legs. The pressure element 8' is in such a position that the outwardly extending portions 92 of the resilient fingers 91a, 91b are located above the flattened portions 93 of the pins 9a', 9b'. In this position the pressure element 8' is in an insertion position. Then, the screw head is inserted through the openings 18 and 86 until the second portion 82 of the pressure element 8' is around the screw head 3. Then, as shown in FIG. 22, the pressure element 8' is moved slightly downward to enter a pre-locking position. Here, the resilient fingers 91a, 91b are first pressed inwards for the outwardly extending portion 92 to move past the flattened portion 93 of the pins. As shown in FIG. 23, the outwardly extending portions 92 then move outward and the flattened portions 93 form an abutment for the pressure element. In this pre-locking position, the tapered outer surface portion of the second portion 82 engages the tapered portion 17 of the receiving part body. Since the pins 9a', 9b' act as a stop, the pre-locking position is secured (i.e., the pressure element 8' does not move back to the insertion position).

Figure 26:
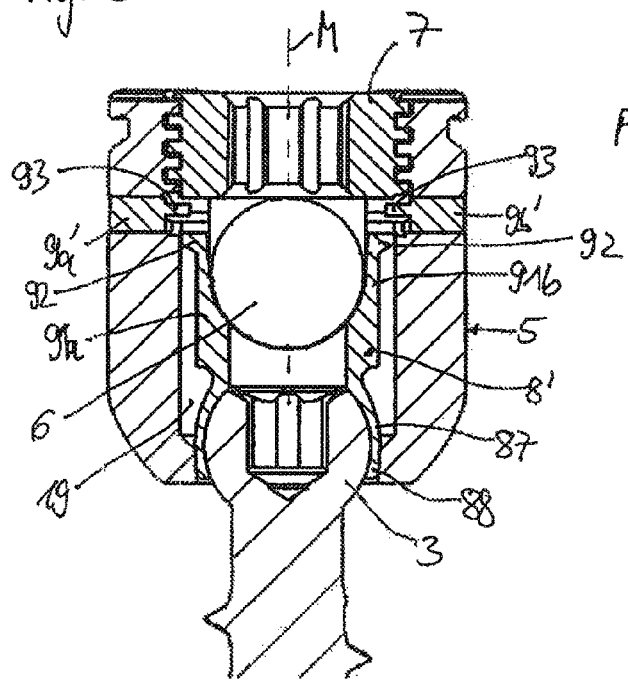
FIG. 26 shows the bone anchoring device of FIG. 20 with the pressure element in the locking position and the head locked.

Inserting the rod and screwing in the inner screw 7 moves the pressure element further down until it achieves a final locking position as shown in FIG. 26.

The clinical use of the bone anchoring device is similar to that of the first embodiment.

Further modifications of the embodiments shown are possible. For example, the head of the bone anchoring element can have any other shape, for example, a cylindrical shape whereby a monoaxial bone screw is provided allowing rotation of the screw element with respect to the receiving part around a single axis. The head 3 can also be, for example, conically shaped, where the hollow interior portion 85 of the pressure element is adapted to this shape. In a further modification, the receiving part body 5, or at least the second portion 82 of the pressure element, is made of a bio-compatible plastic material which provides elasticity to a certain degree. In this case, the slits may be omitted.

Alternatively to the second embodiment a spring portion can be provided, for example in the receiving part body, which may cooperates with a portion of the pressure element. Generally, the pins are only one example of achieving an abutment for the pressure element. Other constructions such as snap rings or various other features may also be utilized.

In one embodiment, the receiving part body can have an inclined open end to allow a greater angulation of the head in one direction.

In one embodiment, the outer surface of the second portion 82 of the pressure element can be tapered, and the second tapered portion 17 of the receiving part body can be inwardly curved.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A receiving part for receiving a rod for coupling the rod to a bone anchoring element, the receiving part comprising:
   a receiving part body having a channel for receiving a rod and defining a bore with a first diameter that provides an accommodation space for accommodating a head of a bone anchoring element, the receiving part body further defining an opening with a second diameter that is smaller than the first diameter for inserting the head, wherein an edge is formed between the bore and the opening; and
   a pressure element at least partially in the accommodation space, the pressure element comprising a first portion having a recess to receive the rod, and a second portion having a flexible portion defining a hollow interior to accommodate and clamp the head and an opening defined by an inner surface of an end region of the second portion to insert the head;
   wherein the pressure element is moveable along a longitudinal axis of the receiving part body from an inserting position to insert the head, to a pre-locking position where an outer surface of the end region of the second portion of the pressure element engages the edge of the receiving part body to clamp the head in the receiving part by a pre-stress exerted by the pressure element, to a locking position to lock the head in the receiving part.

2. The receiving part of claim 1, wherein the pressure element is expandable in the accommodation space in the inserting position.

3. The receiving part of claim 1, wherein a stop contacts the pressure element in the inserting position.

4. The receiving part of claim 1, wherein in the pre-locking position, an outer wall of the pressure element engages a portion of an inner wall of the receiving part body.

5. The receiving part of claim 1, wherein the pressure element is held in the pre-locking position by a spring force.

6. The receiving part of claim 5, wherein the spring force is generated by a spring portion on one of the pressure element or the receiving part body which cooperates with an abutment on the other one of the receiving part body or the pressure element.

7. The receiving part of claim 1, wherein a head of an inserted bone anchoring element is removable from the receiving part body in the insertion position.

8. The receiving part of claim 1, wherein the accommodation space of the receiving part body is substantially cylindrical and has a narrowing portion near the opening.

9. The receiving part of claim 8, wherein the pressure element comprises a narrowing portion on its outer wall which cooperates with the narrowing portion of the accommodation space.

10. The receiving part of claim 9, wherein at least one of the narrowing portion of the receiving part body or the narrowing portion of the pressure element is tapered.

11. The receiving part of claim 10, wherein the respective narrowing portions of the receiving part body and the pressure element are tapered at substantially a same angle.

12. The receiving part of claim 10, wherein the respective narrowing portions of the receiving part body and the pressure element are tapered at different angles.

13. The receiving part of claim 10, wherein the other one of the narrowing portion of the receiving part or the narrowing portion of the pressure element is curved or rounded.

14. The receiving part of claim 13, wherein the narrowing portion of the receiving part body and the narrowing portion of the pressure element are curved or rounded.

15. The receiving part of claim 14, wherein the narrowing portion of the receiving part body comprises two adjacent curved portions having convex curvatures directed towards a central axis of the receiving part and forming a groove therebetween, and wherein the narrowing portion of the pressure element comprises two adjacent curved portions having concave curvatures corresponding to the convex curvatures of the two curved portions of the receiving part body, respectively, and forming a crest therebetween.

16. The receiving part of claim 15, wherein in the pre-locking position an edge of the pressure element engages the groove of the receiving part body, and wherein in the locking position the crest of the pressure element engages the groove of the receiving part body.

17. The receiving part of claim 1, wherein an outer diameter of the flexible portion is smaller than an inner diameter of the accommodation space.

18. The receiving part of claim 17, wherein a maximum outer diameter of the pressure element is smaller than a minimum inner diameter of the accommodation space.

19. The receiving part of claim 1, wherein the second portion of the pressure element has a smaller maximum outer diameter than a maximum outer diameter of the first portion of the pressure element.

20. The receiving part of claim 1, wherein the channel is a U-shaped recess for receiving the rod.

21. The receiving part of claim 1, wherein the pressure element is secured from removal from the receiving part body.

22. The receiving part of claim 1, wherein in the inserting position, the flexible portion of the pressure element is spaced apart from the receiving part body.

23. The receiving part of claim 1, wherein an end of the second portion adjacent to the first portion has an outer diameter that is recessed with respect to an outer diameter of the first portion.

24. A bone anchoring device comprising:
a bone anchoring element having a shaft and a head; and
a receiving part for receiving a rod for coupling the rod to the bone anchoring element, the receiving part comprising:
a receiving part body having a channel for receiving the rod and defining a bore with a first diameter that provides an accommodation space for accommodating the head of the bone anchoring element, the receiving part body further defining an opening with a second diameter that is smaller than the first diameter for inserting the head, wherein an edge is formed between the bore and the opening; and
a pressure element at least partially in the accommodation space, the pressure element comprising a first portion having a recess to receive the rod, and a second portion having a flexible portion defining a hollow interior to accommodate and clamp the head and an opening defined by an inner surface of an end region of the second portion to insert the head;
wherein the pressure element is moveable along a longitudinal axis of the receiving part body from an inserting position to insert the head, to a pre-locking position where an outer surface of the end region of the second portion of the pressure element engages the edge of the receiving part body to clamp the head in the receiving part by a pre-stress exerted by the pressure element on the head, to a locking position to lock the head in the receiving part.

25. The bone anchoring device of claim 24, wherein the pre-stress exerts less force on the head than a force exerted on the head in the locking position.

26. The bone anchoring device of claim 24, wherein in the pre-locking position the bone anchoring element is maintained at a temporary angular position relative to the receiving part by the pre-stress exerted on the head by the pressure element, and wherein in the locking position the bone anchoring element is locked relative to the receiving part by a force exerted by the pressure element on the head in the locking position.

27. The bone anchoring device of claim 24, wherein the head is insertable and removable from the receiving part body in the insertion position, and wherein the flexible portion of the pressure element remains spaced apart from the receiving part body during insertion or removal of the head.

28. The bone anchoring device of claim 24, further comprising:
the rod; and
a closure element for securing the rod in the receiving part.

29. A receiving part for receiving a rod for coupling the rod to a bone anchoring element, the receiving part comprising:
a receiving part body having a channel at a first end for receiving a rod, and defining a bore with a first diameter that provides an accommodation space for accommodating a head of a bone anchoring element, the receiving part body further defining an opening with a second diameter that is smaller than the first diameter at a second end of the receiving part body opposite the first end, wherein an edge is formed between the bore and the opening; and
a pressure element configured to be located at least partially in the receiving part body, the pressure element comprising a first portion having a recess alignable with the channel, and a second portion having a flexible portion defining a hollow interior and an opening defined by an inner surface of an end region of the second portion, the second portion positionable at least partially in the accommodation space, wherein the pressure element is moveable along a longitudinal axis of the receiving part body from an inserting position wherein the flexible portion is in the accommodation space and spaced apart from an inner wall of the receiving part body, to a pre-locking position wherein an outer surface of the end region of the second portion of the pressure element engages the edge of the receiving part body such that the receiving part body exerts a first compressive force on the flexible portion, to a locking position wherein the inner wail of the receiving part body exerts a second compressive force greater than the first compressive force on the flexible portion.

30. A method of coupling a rod to a bone anchoring element via a receiving part, the receiving part comprising a receiving part body having a channel for receiving a rod and defining a bore with a first diameter that provides an accommodation space for accommodating a head of the bone anchoring element, the receiving part further defining an opening with a second diameter that is smaller than the first diameter for inserting the head, wherein an edge is formed between the bore and the opening, and a pressure element at least partially in the accommodation space, the pressure element comprising a first portion having a recess to receive the rod, and a second portion having a flexible portion defining a hollow interior to accommodate and clamp the head and an opening defined by an inner surface of an end region of the second portion to insert the head, the method comprising:

inserting the bone anchoring element into a bone or vertebra;

introducing the head of the bone anchoring element through the openings of the receiving part body and the pressure element into the flexible portion of the pressure element when the pressure element is in an inserting position;

moving the pressure element along a longitudinal axis of the receiving part body to a pre-locking position where an outer surface of the end region of the second portion of the pressure element engages the edge of the receiving part body to clamp the head in the receiving part by a pre-stress exerted by the pressure element;

applying a force on the receiving part body or the bone anchoring element that is greater than a force of the pre-stress to adjust an angular position of the receiving part relative to the bone anchoring element;

inserting the rod into the channel of the receiving part body; and advancing a closure element in the channel to push the rod against the pressure element to move the pressure element further along the longitudinal axis to a locking position, to lock respective positions of the bone anchoring element and the rod relative to the receiving part.

* * * * *

UNITED STATES PATENT AND TRADEMARK OFFICE
CERTIFICATE OF CORRECTION

Page 1 of 1

PATENT NO. : 8,926,671 B2
APPLICATION NO. : 12/709375
DATED : January 6, 2015
INVENTOR(S) : Biedermann et al.

It is certified that error appears in the above-identified patent and that said Letters Patent is hereby corrected as shown below:

In the Claims

Column 11, Claim 29, line 15          Delete "wail"
                                       Insert -- wall --

Signed and Sealed this
Sixth Day of October, 2015

Michelle K. Lee
*Director of the United States Patent and Trademark Office*